(12) United States Patent  (10) Patent No.: US 8,065,160 B1
Gatti et al.  (45) Date of Patent: Nov. 22, 2011

(54) CENTRALIZED PHARMACY BUSINESS METHOD

(75) Inventors: William Gatti, Indiana, PA (US); Gary Duty, Cranberry Township, Butler County, PA (US)

(73) Assignee: Millennium Pharmacy Systems, Inc., Oak Brook, IL (US)

( * ) Notice: Subject to any disclaimer, the term of this patent is extended or adjusted under 35 U.S.C. 154(b) by 991 days.

(21) Appl. No.: 10/134,293

(22) Filed: Apr. 29, 2002

(51) Int. Cl.
  *G06Q 10/00* (2006.01)
(52) U.S. Cl. .................................. 705/2; 705/3
(58) Field of Classification Search .................. 705/1–4, 705/26
  See application file for complete search history.

(56) References Cited

U.S. PATENT DOCUMENTS

| | | | | |
|---|---|---|---|---|
| 5,537,314 | A * | 7/1996 | Kanter | 705/14 |
| 5,832,449 | A * | 11/1998 | Cunningham | 705/3 |
| 5,950,630 | A * | 9/1999 | Portwood et al. | 128/897 |
| 6,493,427 | B1 * | 12/2002 | Kobylevsky et al. | 379/67.1 |
| 2001/0037205 | A1 * | 11/2001 | Joao | 705/1 |
| 2002/0002495 | A1 * | 1/2002 | Ullman | |
| 2002/0032582 | A1 * | 3/2002 | Feeney et al. | 705/2 |
| 2002/0035484 | A1 * | 3/2002 | McCormick | 705/2 |
| 2002/0069088 | A1 | 6/2002 | Berg | 705/3 |
| 2002/0198784 | A1 * | 12/2002 | Shaak et al. | 705/26 |
| 2003/0041107 | A1 * | 2/2003 | Blattner et al. | 709/204 |

OTHER PUBLICATIONS

"Operation of Prescriiption Druges Plan Varioes, Depending upon the Type of System Being Used", Employee Benefit Plan Review, vol. 36, No. 7, p. 20-24, Jan. 1982. From Dialg File 15 (ABI Inform®).*
"Transformation in small doses" by Deanna Bellandi (Non-patent reference).*
"Smaller Pharmacies in Kansas Centralize to Fight Mail-Order Rivals" published on Jul. 14, 2001 by Novelda Sommers. Available in Dialog—File 20-Dialog Global Report. Dialog (Document) No. 17831301.*

* cited by examiner

*Primary Examiner* — Vivek Koppikar
(74) *Attorney, Agent, or Firm* — GTC Law Group LLP & Affiliates

(57) ABSTRACT

A centralized pharmacy business method includes forming a business alliance between a centralized pharmacy, one or more satellite pharmacists/facility directors, and a shipping service. Optionally, the centralized pharmacy and the shipping service are located "end of runway," which means that the shipping service is co-located with or in close proximity to the centralized pharmacy. The satellite pharmacists/facility directors may accrue incentives based on recruiting one or more customer bases. Maintenance prescription orders are received and filled by the centralized pharmacy and delivered to the respective customer base. Acute prescription orders are received and filled by the satellite pharmacy of the pharmacists/facility directors near the customer base and may be delivered to the respective customer base.

9 Claims, 1 Drawing Sheet

CENTRALIZED PHARMACY BUSINESS METHOD

CROSS REFERENCE TO RELATED APPLICATIONS

This patent application claims priority to U.S. patent application Ser. No. 10/062,170, filed Jan. 31, 2002, and which also corresponds to U.S. Provisional Patent Application Ser. No. 60/265,508, filed Jan. 31, 2001, the latter of which is incorporated herein by reference.

DETAILED DESCRIPTION OF THE EMBODIMENTS OF THE INVENTION

Figure 1:
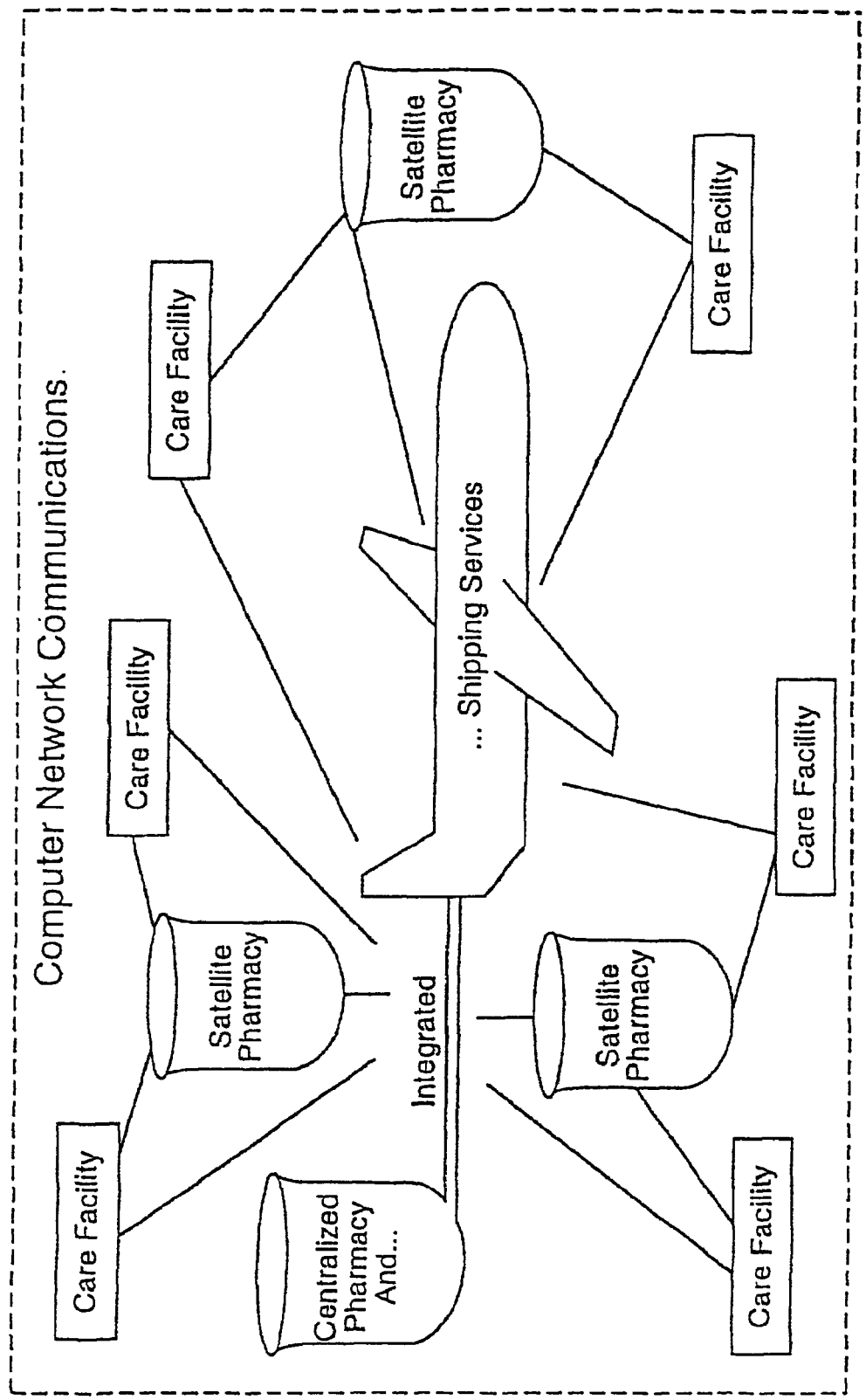
FIG. 1 is a flow diagram illustrating the trifid business method coordinated among a central pharmacy, a satellite pharmacy, and a shipping service.

One embodiment of the present invention is a trifid business method embracing three essential elements, namely, the central pharmacy, the satellite pharmacy and the shipping service. This trifid business model serves any pharmaceutical consumer including individual patients and institutional markets, such as care facilities and hospitals. Within a protocol coordinated by a computer network and the appropriate software, (1) a central pharmacy service and (2) a shipping service provide daily prescription delivery to the consumer, with acute prescriptions being separately delivered by (3) the satellite pharmacy nearby to the consumer. This protocol is illustrated in FIG. 1. The economic force that expands the overall trifid business is the incentive pay that each newly established satellite pharmacy is entitled to based upon the consumer volume brought in by each satellite pharmacist/facility director. Each satellite pharmacist/facility director participant in the trifid business plan thus becomes a "producer/feeder" for the centralized business (long-term and repeat orders), but his or her satellite pharmacy remains a direct provider for acute prescriptions the centralized service cannot readily fill. In one configuration, the trifid business method embraces an integrated central pharmacy and shipping service, positioned "end of runway" (i.e., as near as possible to the shipping point of departure). The preponderance of filled prescriptions for each care facility arrives in overnight and/or routine shipments from the central pharmacy, and the satellite pharmacies fill the new and modified prescriptions on an acute need basis.

According to one embodiment of the invention, stated a little differently, there is provided an integrated trifid pharmacy distribution system for a variety of end use customers. The centralized pharmacy or "hub" provides long-term maintenance prescriptions to a customer base with the aid of a daily shipping service. The hub contracts directly (or indirectly) with satellite pharmacists/facility directors. The respective satellite pharmacies provide acute prescriptions to the customer base through regular delivery means. Customer bases may include long-term care facilities, hospitals, institutions, and/or private residences. Communication between the hub and the satellites is accomplished through a coordinated computer network, possibly enabled by Internet connectivity.

The centralized "hub" pharmacy is the keystone of the operation. It can house an enormous quantity of maintenance and "fast mover" medications because of the high volume of orders filled daily. The enormous quantity of medications is proportionate to enormous saving in drug costs. Many pharmaceutical companies provide discounts on wholesale medication costs that may increate with the quantity of medication purchased. Equally important are the similar economic benefits that accrue from formulary-driven increases in manufacturer's market share.

The centralized pharmacy and the shipping service may be located "end of runway," which means that the shipping service is co-located with or in close proximity to the centralized pharmacy. Close proximity means that the centralized pharmacy and the shipping service are within about a one-hour surface traveling time from each other. This arrangement decreases costs because prescriptions only need to be shipped on way, i.e., from the end of runway directly to the customer base. The arrangement also decreases prescription delivery time because the filled prescription orders can be easily and quickly loaded onto carriers by the shipping service.

Satellite pharmacists (producers) receive many benefits for participating in the system. Potentially, they accrue incentives for recruiting other satellite pharmacist and/or customer bases. In any case, the hub pharmacy distributes a percentage of profits to the producer based on total volume generated from the producer's recruited customer base. Also, when applicable, the first producer receives a percentage of profits based on total sale volume generated from the customer base of a second producer recruited by the first producer, and so on. The incentives thus multiply, generating more profit incentives as more customer bases and/or additional producers are recruited. Second, by not having to fill maintenance and long-term orders for a large customer base, a satellite pharmacist/facility director can drastically reduce his or her cumbersome and expensive inventory. Third, the decrease in inventory of maintenance medications allows a satellite pharmacist/facility director to stock less frequently used, but still required, medications. Fourth, the technician and pharmacy staff needs of the satellite pharmacist/facility director decrease because the workload related to providing maintenance medications to a customer base decreases. This allows for decreased pharmacy man hours with an increase in both profitability and pharmaceutical care quality, because satellite pharmacist/facility directors have more time to evaluate and to manage acute prescription filling while steady revenues can be counted on from hub sales.

The customer base also receives many benefits from this system. First, because the satellite pharmacies will generally have more room to stock infrequent medications, it is less likely that an acute need medication would be unavailable. Second, the institutionalized customer base can depend on regularly scheduled drug delivery for its patients from the hub pharmacy. Staff time management is greatly improved because staff can plan for a majority of drug shipments to arrive only once a day. Third, the private residence base can also benefit from the above-described prescription delivery system. Many people on maintenance medication are elderly, incapacitated, without transportation, etc. Because it can be difficult for them to travel to the local pharmacy, residential medication delivery is a helpful way to improve prescription compliance.

The aforementioned benefits of this system are not limited. The embodiment of this invention that follows illuminates the many advantages of a centralized pharmacy business system.

In essence, the centralized "hub" pharmacy, the satellite pharmacists/facility directors and the shipping service work in concert to provide accurate, efficient, and cost-effective pharmaceutical care to customer bases. The satellite pharmacists/facility directors (producers) may enter the system on an incentive basis. The producers receive a percentage of the total profits from the total volume of sales generated by each customer base they recruit. Thus, although the producers take no direct part in providing maintenance medications to their customer base, they still receive a profit from the maintenance business thus generated. The satellite pharmacies are mostly responsible for providing acute medications to the customer base. Acute prescriptions may include new, sort-term medication orders such as orders for a one-week cycle of an antibiotic or a few days' worth of pain medication. An acute prescription may also be an adjusted therapeutic strategy such as an increased or decreased dose and/or strength of a maintenance drug or an altered medication route of administration.

A fully operational system involving one institutional care customer base, one satellite pharmacist/facility director, the hub pharmacy and the shipping system is orchestrated as follows. A physician or authorized person at the customer base scans or enters prescriptions for their patients into the pharmacy system's coordinated computer network using an optional hand-held prescribing device. Additionally, orders may be automatically renewed via the computer on a scheduled basis. A pharmacist at the hub receives the prescriptions and verifies them for accuracy, proper indication, etc. For maintenance medications, prescription labels are generated with numeric bar code indicators at the hub. The order is filled with the use of filling trays and checked by a pharmacist. Checked orders are placed in a customer base specific tote and are scanned for customer base specific completeness and accuracy. If complete and accurate, the tote is delivered by the shipping service to the designated customer base. Upon arrival at the base, the tote is scanned again for accuracy and completeness. After scanning, the medications are delivered to the appropriate patients at the customer base.

If an order from the customer base is for an acute prescription, the pharmacist at the hub sends the order through the computer network to a producer's satellite pharmacy closest to the customer base. Alternatively, the acute prescription order may be sent directly from the customer base to the satellite pharmacy. Proper prescription dispensing procedures are followed as well as the additional bar code scanning step for "customer base" completeness and accuracy. Once completed, the order is immediately delivered to the base through regular delivery means. Upon arrival, the order is scanned again for accuracy and completeness. After scanning, the medication(s) are delivered to the appropriate patient at the base.

As one can imagine, the possibilities for this coordinated system are endless. Because of numerous advantages and incentives, an ever-growing network of pharmacies and customer bases can be grown. The larger the network, the more efficient and cost-effective the system will become, thus creating improved and expedient customer care at a reduced price and greater overall profitability.

Generally, although not always, the producer is the satellite pharmacist/facility director or an individual who bears the individual contractual rights and obligations. For this reason, the distinction has been carefully made, above, between the satellite pharmacist/facility director and the satellite pharmacy itself.

It will be understood by those skilled in the art that while the foregoing description sets forth in detail embodiments of the present invention, modifications, additions, and changes might be made thereto without departing from the spirit and scope of the invention.

Having thus described embodiments of the invention with the detail and particularity required by the Patent Laws, what is desired to be protected by Letters Patent is set forth in the following claims.

The invention claimed is:

1. A computerized method for fulfilling a pharmacy prescription order, the method comprising:
receiving, via a computer network, one or more maintenance prescription orders on a first computer at a central pharmacy from a first customer base, wherein a maintenance prescription order is one that is prescribed on a scheduled and routine basis;
receiving, via the computer network, one or more acute prescription orders on the first computer at the central pharmacy from the first customer base, wherein an acute prescription order is one that is identified as needed immediately, within a time period inconsistent with an overnight delivery, said prescription needed for a limited and defined duration;
accessing the one or more acute prescription orders via the computer network with a second computer associated with a first satellite pharmacy, wherein the first satellite pharmacy is one of a plurality of satellite pharmacies, wherein each of the plurality of satellite pharmacies has a producer that has a contractual relationship with the central pharmacy, and wherein, of the plurality of satellite pharmacies, determining the first satellite pharmacy is located closest to the first customer base;
filling the one or more maintenance prescription orders at the central pharmacy; and
delivering the one or more filled maintenance prescription orders from the central pharmacy to the first customer base via a first shipment;
wherein the one or more acute prescription orders are filled at the first satellite pharmacy and delivered from the first satellite pharmacy to the first customer base via a second shipment.

2. The computerized method for fulfilling a pharmacy prescription order according to claim 1 further comprising recruiting one or more customer bases by said producer, wherein said producers accrue incentives based on said recruiting.

3. The computerized method for fulfilling a pharmacy prescription order according to claim 2 wherein said incentives derive from the centralized pharmacy's distributing a percentage of profits to said producers based on total sales volume generated from said one or more customer bases.

4. The computerized method for fulfilling a pharmacy prescription order according to claim 2 wherein said incentives further include additional remuneration to a first producer which recruits a second producer or the second producer's customer base.

5. The computerized method for fulfilling a pharmacy prescription order according to claim 1 wherein said customer base is selected from a group consisting of long-term care facilities, hospitals, institutions and private residences.

6. The computerized method for fulfilling a pharmacy prescription order according to claim 1 wherein acute prescription orders are new, short-term medication orders.

7. The computerized method for fulfilling a pharmacy prescription order according to claim 1 wherein acute prescription orders are adjusted medication orders.

8. The computerized method for fulfilling a pharmacy prescription order according to claim 1 wherein maintenance prescription orders are long-term medication orders.

9. The computerized method for fulfilling a pharmacy prescription order according to claim 1 wherein the centralized pharmacy is located within about a one-hour surface traveling time from a shipping service.

* * * * *